(12) United States Patent
Liu et al.

(10) Patent No.: US 10,736,984 B2
(45) Date of Patent: Aug. 11, 2020

(54) PHOTOCATALYST STERILIZATION DEVICE AND REFRIGERATOR INCLUDING THE SAME

(71) Applicant: SHENZHEN H&T INTELLIGENT CONTROL CO., LTD., Shenzhen (CN)

(72) Inventors: Quansheng Liu, Shenzhen (CN); Xinhua Jiang, Shenzhen (CN); Wenjun Lan, Shenzhen (CN); Yanwen Liu, Shenzhen (CN)

(73) Assignee: SHENZHEN H&T INTELLIGENT CONTROL CO., LTD., Shenzhen (CN)

( * ) Notice: Subject to any disclaimer, the term of this patent is extended or adjusted under 35 U.S.C. 154(b) by 0 days.

(21) Appl. No.: 16/175,984

(22) Filed: Oct. 31, 2018

(65) Prior Publication Data
US 2019/0374670 A1 Dec. 12, 2019

Related U.S. Application Data

(63) Continuation of application No. PCT/CN2018/090266, filed on Jun. 7, 2018.

(51) Int. Cl.
*A61L 9/20* (2006.01)

(52) U.S. Cl.
CPC .......... *A61L 9/205* (2013.01); *A61L 2209/111* (2013.01); *A61L 2209/12* (2013.01); *A61L 2209/14* (2013.01); *F25D 2317/0417* (2013.01)

(58) Field of Classification Search
CPC .. A61L 9/205; A61L 2209/14; A61L 2209/12; A61L 2209/111; F25D 2317/0417
See application file for complete search history.

(56) References Cited

U.S. PATENT DOCUMENTS

| | | | | |
|---|---|---|---|---|
| 5,015,442 | A * | 5/1991 | Hirai | A61L 9/015 261/DIG. 88 |
| 2018/0272024 | A1* | 9/2018 | Seo | A61L 9/20 |
| 2019/0105422 | A1* | 4/2019 | Jeong | A61L 9/205 |

FOREIGN PATENT DOCUMENTS

| | | |
|---|---|---|
| CN | 2653399 Y | 11/2004 |
| CN | 2659436 Y | 12/2004 |
| CN | 103623452 U | 3/2014 |
| CN | 103983069 A | 8/2014 |

(Continued)

*Primary Examiner* — Sean E Conley
*Assistant Examiner* — Brendan A Hensel
(74) *Attorney, Agent, or Firm* — IPro, PLLC

(57) ABSTRACT

A photocatalyst sterilization device includes a housing, wherein the housing includes a first receiving chamber and a second receiving chamber that are in communication with each other, the first receiving chamber receives a photocatalyst layer and a light source assembly configured to irradiate the photocatalyst layer, the second receiving chamber receives an axial-flow fan; and an air inlet and an air outlet are defined in the same surface of the housing, one of the air inlet and the air outlet is corresponded to the first receiving chamber in position, the other one of the air inlet and the air outlet is corresponded to the second receiving chamber in position, and a direction in which the axial-flow fan suctions air via the air inlet is parallel to a direction of irradiation of the light source assembly.

9 Claims, 5 Drawing Sheets

(56) References Cited

FOREIGN PATENT DOCUMENTS

| | | |
|---|---|---|
| CN | 106247748 A | 12/2016 |
| CN | 206842184 U | 1/2018 |
| CN | 207778939 U | 8/2018 |
| CU | 207293100 U | 5/2018 |
| JP | H11276563 A | 10/1999 |

* cited by examiner

PHOTOCATALYST STERILIZATION DEVICE AND REFRIGERATOR INCLUDING THE SAME

This disclosure is a continuation of International Patent Application No. PCT/CN2018/090266, filed on Jun. 7, 2018, the entire contents of which are incorporated herein by reference.

TECHNICAL FIELD

The present disclosure relates to the technical field of household appliances, and in particular, relates to a photocatalyst sterilization device and a refrigerator including the photocatalyst sterilization device.

BACKGROUND

Refrigerators are indispensable household appliances in most families. In the daily life, various vegetables, meats and fruits need to be stored in the refrigerator for fresh-keeping and cooling. The storage cabinet of the refrigerator generally has a temperature of 2-8° C. However, under such condition, there may still be some bacteria in the stored food, which will affect the food preservation effect. Some foods even release stench that spread throughout the entire storage cabinet, creating a vicious cycle. Therefore, an effective sterilization and fresh-keeping technology is an important subject in the field of refrigerator cold storage.

At present, a sterilization device may be arranged on the air duct of an air-cooled refrigerator to remove the microbial bacteria and stench caused by decayed foods.

SUMMARY

An embodiment of the present disclosure provides a photocatalyst sterilization device, the photocatalyst sterilization device including a housing; wherein the housing includes a first receiving chamber and a second receiving chamber that are in communication with each other, the first receiving chamber receives a photocatalyst layer and a light source assembly configured to irradiate the photocatalyst layer, the second receiving chamber receives an axial-flow fan; wherein an air inlet and an air outlet are defined in the same surface of the housing, one of the air inlet and the air outlet is corresponded to the first receiving chamber in position, the other one of the air inlet and the air outlet is corresponded to the second receiving chamber in position, and a direction in which the axial-flow fan suctions air via the air inlet is parallel to a direction of irradiation of the light source assembly.

Another embodiment of the present disclosure provides a refrigerator, the refrigerator including a storage cabinet; wherein the storage cabinet includes a photocatalyst sterilization device, the photocatalyst sterilization device including a housing; wherein the housing includes a first receiving chamber and a second receiving chamber that are in communication with each other, the first receiving chamber receives a photocatalyst layer and a light source assembly configured to irradiate the photocatalyst layer, the second receiving chamber receives an axial-flow fan; wherein an air inlet and an air outlet are defined in the same surface of the housing, one of the air inlet and the air outlet is corresponded to the first receiving chamber in position, the other one of the air inlet and the air outlet is corresponded to the second receiving chamber in position, and a direction in which the axial-flow fan suctions air via the air inlet is parallel to a direction of irradiation of the light source assembly.

BRIEF DESCRIPTION OF THE DRAWINGS

For a clearer description of the technical solutions according to the embodiments of the present disclosure, brief description is given with reference to the accompanying drawings for illustrating the embodiments hereinafter. Apparently, the accompanying drawings described hereinafter only illustrate some embodiments of the present disclosure, and other accompanying drawings may also be derived based on these accompanying drawings.

DETAILED DESCRIPTION

For better understanding of the present disclosure, the present disclosure is described in detail with reference to attached drawings and specific embodiments. It should be noted that, when an element is defined as "being secured or fixed to" another element, the element may be directly positioned on the element or one or more centered elements may be present therebetween. When an element is defined as "being connected or coupled to" another element, the element may be directly connected or coupled to the element or one or more centered elements may be present therebetween. As used herein, the terms "vertical", "horizontal", "left", "right", and similar expressions are for illustration purposes.

Unless the context clearly requires otherwise, throughout the specification and the claims, technical and scientific terms used herein denote the meaning as commonly understood by a person skilled in the art. Additionally, the terms used in the specification of the present disclosure are merely for describing the embodiments of the present disclosure, but are not intended to limit the present disclosure. As used herein, the term "and/or" in reference to a list of two or more items covers all of the following interpretations of the term: any of the items in the list, all of the items in the list and any combination of the items in the list.

Figure 1:
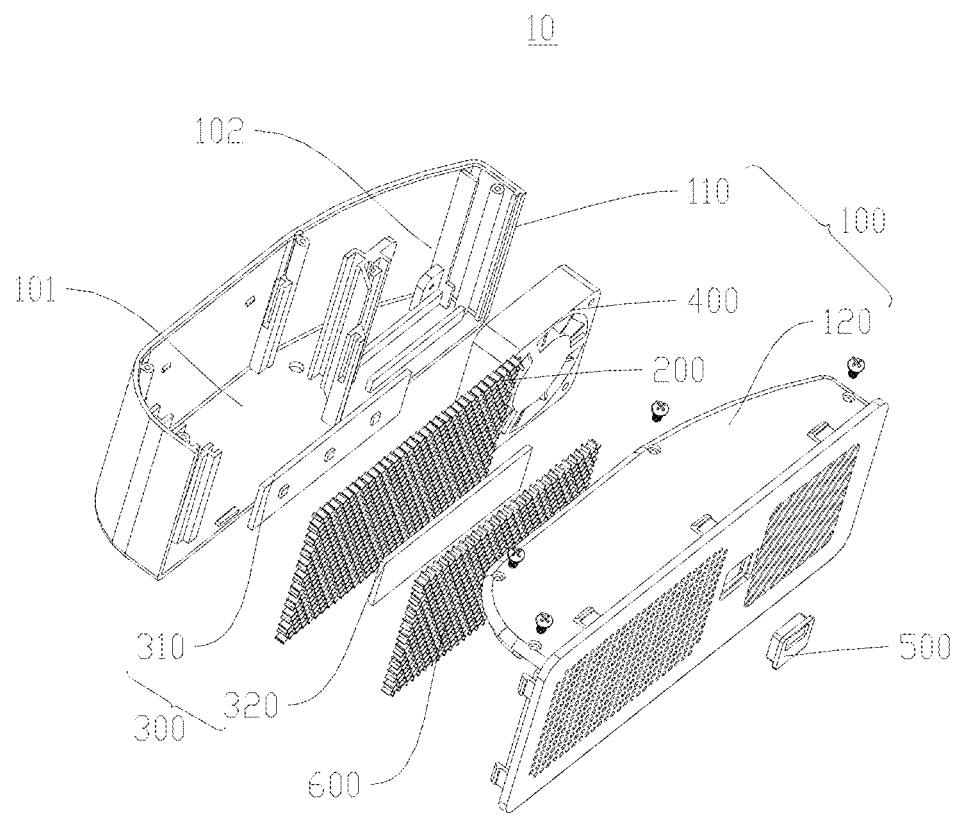
FIG. 1 is an exploded structural view of a photocatalyst sterilization device according to an embodiment of the present disclosure.

Referring to FIG. 1, FIG. 1 is an exploded structural view of a photocatalyst sterilization device according to an embodiment of the present disclosure. The photocatalyst sterilization device 10 includes a housing 100, a photocatalyst layer 200, a light source assembly 300 and an axial-flow fan 400. The photocatalyst layer 200, the light source assembly 300 and the axial-flow fan 400 are all received in the housing 100.

In some embodiments, the housing 100 includes a first housing 110 and a second housing 120 that are secured to each other, wherein the first housing 110 and the second housing 120 enclose to form an inner space of the housing 100. The housing 100 includes a first receiving chamber 101 and a second receiving chamber 102 that are in communication with each other. The photocatalyst layer 200 and the light source assembly 300 irradiating the photocatalyst layer 200 are positioned in the first receiving chamber 101. The axial-flow fan 400 is positioned in the second receiving chamber 102.

Figure 2:
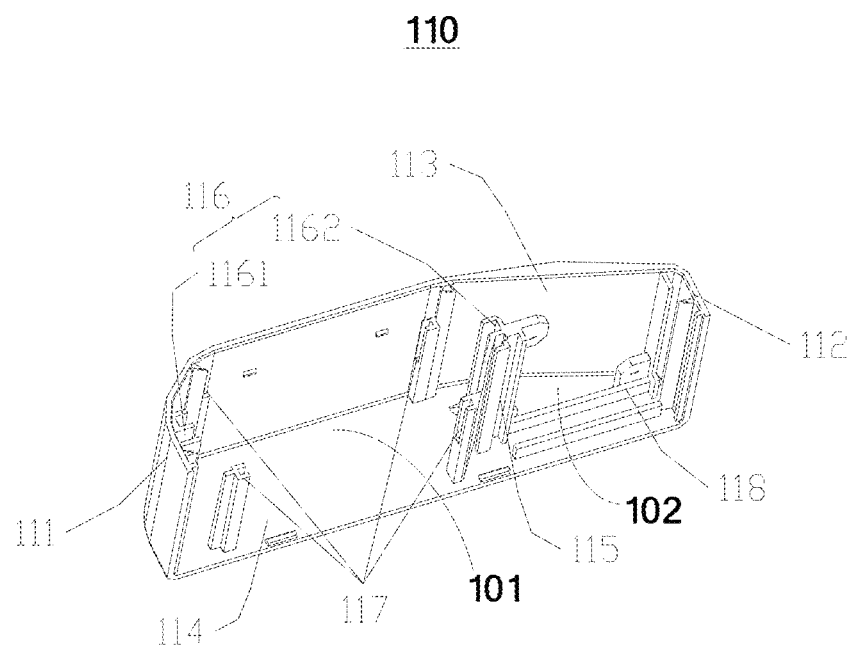
FIG. 2 is a schematic structural view of a first housing of the photocatalyst sterilization device shown in FIG. 1.

Referring also to FIG. 2, the first housing 110 includes a first side wall 111, a second side wall 112, a housing rear wall 113 and a housing bottom wall 114. The housing rear wall 113 is connected to the first side wall 111 and the second side wall 112. The housing bottom wall 114 is connected to the first side wall 111 and the second side wall 112. The first housing 110 further includes an isolating plate 115 projecting inwardly from the housing bottom wall 114, wherein the isolating plate 115 divides the inner space of the housing 100 into the first receiving chamber 101 and the second receiving chamber 102.

A first slot 116 and a second slot 117 are arranged on the first housing 110 in the first receiving chamber 101. The first slot 116 is configured to mount the photocatalyst layer 200. The second slot 117 is configured to mount the light source assembly 300.

The first slot 116 includes a first catch portion 1161 and a second catch portion 1162, wherein the first catch portion 1161 is arrange on the first side wall 111 inwardly projecting towards the first receiving chamber 101, and the second catch portion 1162 is arrange on the isolating plate 115 inwardly projecting towards the first receiving chamber 101. Two sides of the photocatalyst layer 200 are respectively inserted into the first catch portion 1161 and the second catch portion 1162 and are fixed in the first receiving chamber 101, which effectively utilizes an inner space of the first receiving chamber 101.

In other embodiments, the first slot 116 may also be arranged on the housing bottom wall 114 inwardly projecting towards the first receiving chamber 101. The bottom of the photocatalyst layer 200 is inserted into the first slot 116, and the photocatalyst layer 200 may be fixed in the first receiving chamber 101 likewise. The depth of the first slot 116 is determined by the height of the photocatalyst layer 200.

The structure of the second slot 117 is similar to the structure of the first slot 116. The difference lies in that the catch portion of the second slot 117 may also be arranged on the housing rear wall 113 inwardly projecting towards the first receiving chamber 101.

A holder 118 is arranged on the first housing 110 in the second receiving chamber 102 and configured to mount the axial-flow fan 400, wherein the axial-flow fan 400 may be fixed to the holder 118 via a screw. Nevertheless, the axial-flow fan 400 may be fixed in the second receiving chamber 102 in other manners, which may be selected or changed by a person skilled in the art.

Figure 3:
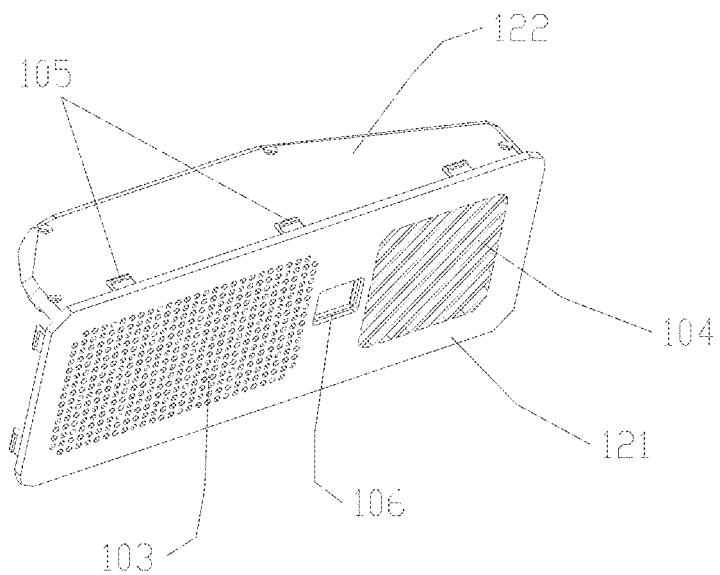
FIG. 3 is a schematic structural view of a second housing of the photocatalyst sterilization device shown in FIG. 1.

As shown in FIG. 3, the second housing 120 includes a housing front wall 121 and a housing upper wall 122. An air inlet 103 and an air outlet 104 are defined on the housing front wall 121. The air inlet 103 corresponds to the first receiving chamber 101 in position, and the air outlet 104 corresponds to the second receiving chamber 103 in position. The air inlet 103 and the air outlet 104 are both designed to have small and fine grids to block impurities having a large particle size from entering the device 10, in case of affecting operation of the device 10.

A plurality of snaps 105 are arranged at an edge of the housing front wall 121. Through the snaps 105, the entire photocatalyst sterilization device 10 may be fixed and hold in a device to be sterilized, which is convenient for mounting and replacement.

In some embodiments, the first housing 110 and the second housing 120 are both made of a food-grade UV-protective material. In this way, the service life of the photocatalyst sterilization device 10 is improved, and the photocatalyst sterilization device 10 may be placed into a food storage device, for example, a refrigerator or a heating chamber.

The photocatalyst layer 200 includes a photocatalyst medium and a photocatalyst carrier configured to carry the photocatalyst medium. For example, the photocatalyst medium may be $TiO_2$, $ZnO$, $CdS$, $WO_3$, $Fe_2O_3$, $PbS$, $SnO_2$, $ZnS$, $SrTiO_3$ or $SiO_2$ or the like, and the photocatalyst carrier may be a metal foam of Ni, Fe, Al, Cr or the like, or may be a non-woven fabric, cellular ceramic substrate or other porous substance, which has a feature of high gas permeability and great specific surface area, and may reduce the volume of the photocatalyst sterilization device 10 effectively.

The light source assembly 300 includes a light source. The light source may be a UV light-emitting diode (having a wavelength of 320-420 nm), a blue light-emitting diode (having a wavelength of 455-492 nm) or other light source that is capable of exciting the photocatalyst medium. According to the actual needs, the light source assembly 300 may further include a light source substrate and/or a heat dissipation plate.

Figure 4:
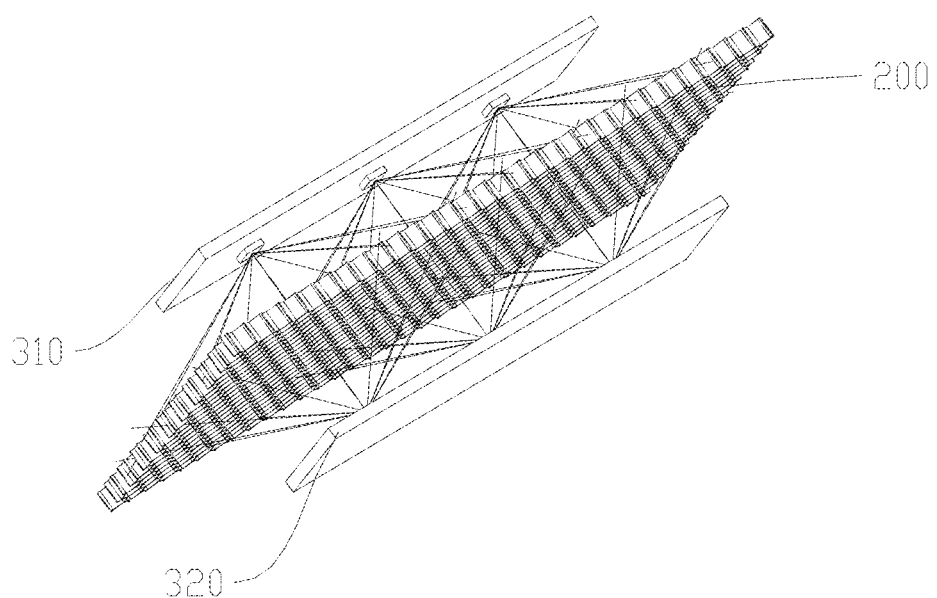
FIG. 4 is a schematic structural view of a photocatalyst layer and a light source assembly of the photocatalyst sterilization device shown in FIG. 1.

In some embodiments, the light source assembly 300 includes a first light source assembly 310 and a second light source assembly 320. As shown in FIG. 4, the first light source assembly 310 and the second light source assembly 320 are oppositely arranged on two sides of the photocatalyst layer 200, such that the light emitted by the light source maximally irradiates the photocatalyst layer 200, and thus the utilization rate of the photocatalyst layer 200 is improved.

Figure 5:
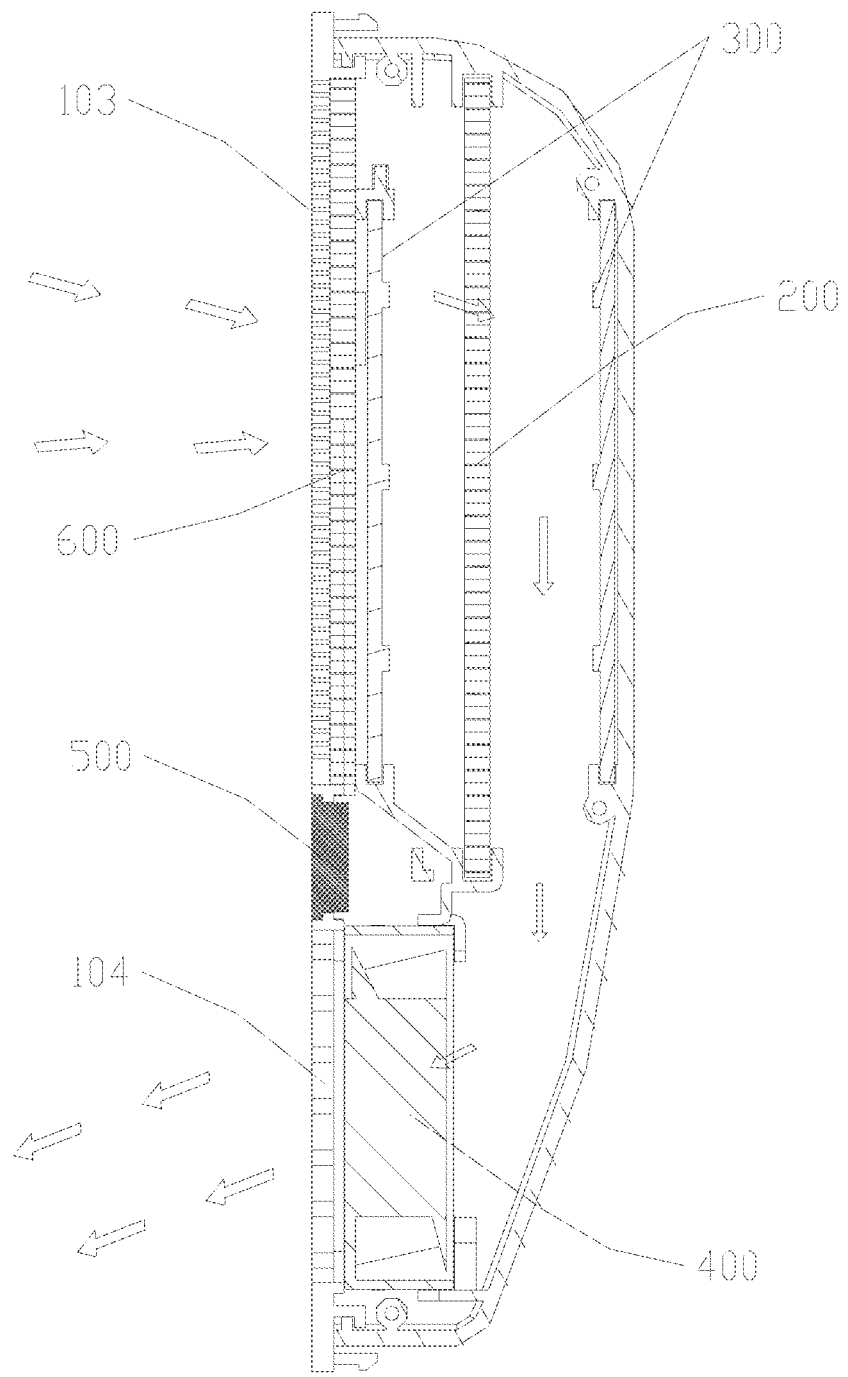
FIG. 5 is a cross-sectional view of the photocatalyst sterilization device shown in FIG. 1.

The axial-flow fan 400 is a fan whose rotation shaft is parallel to the direction of the air flow. As illustrated in FIG. 5, a direction in which the axial-flow fan 400 suctions air via the air inlet 103 is parallel to a direction of irradiation of the light source assembly 300. That is, the direction in which the axial-flow fan 400 suctions air via the air inlet 103 is vertical to a mounting direction of the photocatalyst layer 200, such that the suctioned air may pass through the photocatalyst layer 200 totally. In addition, the air inlet 103 and the air outlet 104 are in the same plane, thereby reducing the thickness of the photocatalyst sterilization device 10 and achieving a compact structure.

After the photocatalyst sterilization device 10 is powered on, with the irradiation of the light source in the light source assembly 300, electrons and holes are generated on the surface of the photocatalyst layer 200. After the electrons and holes are in contact with moisture and oxygen in the air, hydroxyl radicals and negative oxygen groups having strong oxidation are formed. As such, the bacteria, viruses and smells and the like hazardous substances are quickly oxidized and decomposed to become non-hazardous carbon dioxide and water under the effect of the strong oxidant, thereby achieving an effect of purification and sterilization.

The axial-flow fan 400 rotates to form a strong circulating air flow. After the external air is suctioned via the air inlet 103, the external air passes through the first receiving chamber 101 and the second receiving chamber 102 which is in communication with the first receiving chamber 101, and then is exhausted via the air outlet 104. In the above circulation path, the air is purified in the first receiving chamber 101, and thus the purified air is directly exhausted from the air outlet 104. Therefore, the sterilization effect is good.

In other alternative embodiments, the air inlet 103 corresponds to the second receiving chamber 102 in position, and the air outlet 104 corresponds to the first receiving chamber 101 in position. The axial-flow fan 400 rotates to form a strong circulating air flow. After the external air is suctioned via the air inlet 103, the external air passes through the second receiving chamber 102 and the first receiving chamber 101 which is in communication with the second receiving chamber 102, and is purified in the first receiving chamber 101. Finally, the purified air is exhausted from the air outlet 104.

Referring back to FIG. 1, in an embodiment, the photocatalyst sterilization device 10 further includes a biological sensor 500, wherein the biological sensor 500 is exposed outside the housing 100. Exemplarily, a third slot 106 may be arranged on the housing front wall 121 and configured to mount the biological sensor 500, such that the biological sensor 500 is located on the same surface as the air inlet 103 and the air outlet 104 (see FIG. 3).

The biological sensor 500 may detect a concentration of a hazardous bacterium in the external environment quickly and accurately. In practice, a control board of the photocatalyst sterilization device 10 or a control board of a device having the photocatalyst sterilization device 10 may control the light source assembly 300 and the axial-flow fan 400 turn-on or turn-off according to the detection data of the biological sensor 500. In this way, intelligent sterilization is practiced, and energy saving and environment protection are achieved.

In an embodiment, the photocatalyst sterilization device 10 further includes a pre-filter sieve 600, configured to further block the impurities in the external environment from entering the device. When the air inlet 103 corresponds to the first receiving chamber 101 in position, the pre-filter sieve 600 is arranged at a position proximal to the air inlet 103 inside the first receiving chamber 101; and when the air inlet 103 corresponds to the second receiving chamber 102 in position, the pre-filter sieve 600 is arranged at a position proximal to the air inlet 103 inside the second receiving chamber 102.

In the embodiment of the present disclosure, the housing 100 of the photocatalyst sterilization device 10 includes the first receiving chamber 101 and the second receiving chamber 102 that are in communication with each other; the photocatalyst layer 200 and the light source assembly 300 irradiating the photocatalyst layer 200 are both received in the first receiving chamber 101; the axial-flow fan 400 is received in the second receiving chamber 102, wherein the axial-flow fan 400 rotates to form a circulating air flow, and the photocatalyst sterilization device 10 is not limited to be mounted in an air passage of the refrigerator; the air inlet 103 and the air outlet 104 are formed on the same surface of the housing 100, such that the thickness of the photocatalyst sterilization device 10 is reduced and the structure is compact, wherein the air inlet 103 and the air outlet 104 respectively correspond to different receiving chambers, the direction in which the axial-flow fan 400 suctions air via the air inlet 103 is parallel to the irradiation direction of the light source assembly 300, after the external air is suctioned from the air inlet 103, it may totally pass through the photocatalyst layer 200 and then is purified in the first receiving chamber 101, and finally the purified air is directly exhausted from the air outlet 104, thereby achieving a good sterilization effect.

Figure 6:
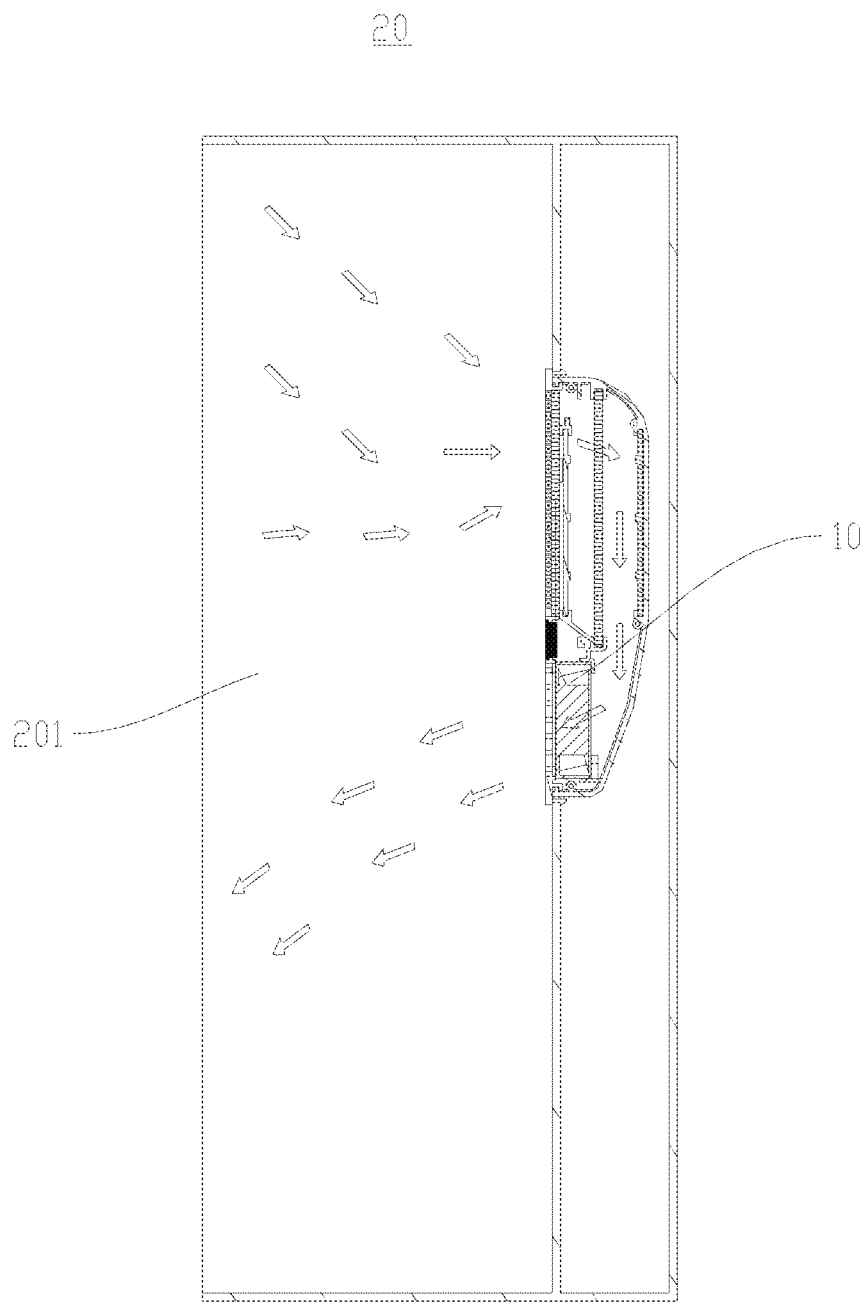
FIG. 6 is a schematic structural view of a refrigerator according to an embodiment of the present disclosure.

An embodiment of the present disclosure further provides a refrigerator 20. As shown in FIG. 6, the refrigerator 20 includes a storage cabinet 201, wherein the storage cabinet 201 includes the photocatalyst sterilization device 10 as described above. The photocatalyst sterilization device 10 may be fixed to an inner wall of the storage cabinet 201 via locking screws, thermal fusion or adhesive. When the axial-flow fan 400 of the photocatalyst sterilization device 10 rotates, the entire storage cabinet 201 may achieve a uniform sterilization effect.

Figure 7:
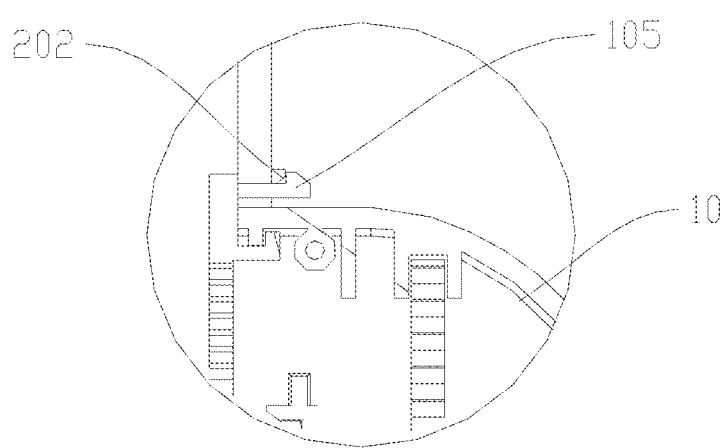
FIG. 7 is a partially enlarged view of a refrigerator according to another embodiment of the present disclosure.

As shown in FIG. 7, in another embodiment, a snap 105 is arranged at an edge of the photocatalyst sterilization device 10. The inner wall of the storage cabinet 201 includes a mounting slot 202 corresponding to the snap 105 in shape and position. The photocatalyst sterilization device 10 may be fixed to the inner wall of the storage cabinet 201 via the snap 105, which is convenient for mounting and replacement.

A person skilled in the art should understand that the photocatalyst sterilization device 10 according to the embodiments of the present disclosure is not limited to apply to a refrigerator and may also be applied to other devices such as a heating chamber, an air purifier or a safe or the like.

It should be noted that the specification and drawings of the present disclosure illustrate exemplary embodiments of the present disclosure. However, the present disclosure may be implemented in different manners, and is not limited to the embodiments described in the specification. The embodiments described are not intended to limit the present disclosure, but are directed to rendering a thorough and comprehensive understanding of the present disclosure. In addition, the technical features described above may incorporate and combine with each other to derive various embodiments not illustrated in the above specification, and such derived embodiments shall all be deemed as falling within the scope of the disclosure contained in the specification of the present disclosure. Further, a person skilled in the art may make improvements or variations according to the above description, and such improvements or variations shall all fall within the protection scope as defined by the claims of the present disclosure.

What is claimed is:

1. A photocatalyst sterilization device, comprising a housing; wherein
the housing comprises a housing front wall, a first side wall, a second side wall opposite to the first side wall, and a housing bottom wall, the housing bottom wall is connected to the first side wall and the second side wall, an isolating plate is projecting inwardly from the housing bottom wall, and divides an inner space of the housing into a first receiving chamber and a second receiving chamber that are in communication with each other, the first receiving chamber and the second receiving chamber are sequentially arranged along a direction from the first side wall to the second side wall;
a first catch portion is arranged on the first side wall inwardly projecting towards the first receiving chamber, a second catch portion is arranged on the isolating plate inwardly projecting towards the first receiving chamber, a photocatalyst layer and a light source assembly configured to irradiate the photocatalyst layer are received in the first receiving chamber, and the photocatalyst layer is mounted between the first catch portion and the second catch portion, an axial-flow fan is fastened within the second receiving chamber;

an air inlet and an air outlet are defined in the housing front wall, one of the air inlet and the air outlet is corresponded to the photocatalyst layer and the light source assembly in position, the other one of the air inlet and the air outlet is corresponded to the axial-flow fan in position, and a direction in which the axial-flow fan suctions air via the air inlet is parallel to a direction of irradiation of the light source assembly toward the photocatalyst layer.

2. The photocatalyst sterilization device according to claim 1, further comprising:

a biological sensor, wherein the biological sensor is exposed outside the housing.

3. The photocatalyst sterilization device according to claim 1, further comprising:

a pre-filter sieve, wherein the pre-filter sieve is arranged at a position proximal to the air inlet inside the first receiving chamber or the second receiving chamber.

4. The photocatalyst sterilization device according to claim 1, wherein the light source assembly comprises a first light source assembly and a second light source assembly, the first light source assembly and the second light source assembly are oppositely arranged on two sides of the photocatalyst layer.

5. A refrigerator, comprising a storage cabinet; wherein the storage cabinet comprises a photocatalyst sterilization device, the photocatalyst sterilization device comprising a housing;

wherein the housing comprises a housing front wall, a first side wall, a second side wall opposite to the first side wall, and a housing bottom wall, the housing bottom wall is connected to the first side wall and the second side wall, an isolating plate is projecting inwardly from the housing bottom wall, and divides an inner space of the housing into a first receiving chamber and a second receiving chamber that are in communication with each other, the first receiving chamber and the second receiving chamber are sequentially arranged along a direction from the first side wall to the second side wall;

a first catch portion is arranged on the first side wall inwardly projecting towards the first receiving chamber, a second catch portion is arranged on the isolating plate inwardly projecting towards the first receiving chamber, a photocatalyst layer and a light source assembly configured to irradiate the photocatalyst layer are received in the first receiving chamber, and the photocatalyst layer is mounted between the first catch portion and the second catch portion, an axial-flow fan is fastened within the second receiving chamber;

an air inlet and an air outlet are defined in the housing front wall, one of the air inlet and the air outlet is corresponded to the photocatalyst layer and the light source assembly in position, the other one of the air inlet and the air outlet is corresponded to the axial-flow fan in position, and a direction in which the axial-flow fan suctions air via the air inlet is parallel to a direction of irradiation of the light source assembly toward the photocatalyst layer.

6. The refrigerator according to claim 5, the photocatalyst sterilization device further comprising:

a biological sensor, wherein the biological sensor is exposed outside the housing.

7. The refrigerator according to claim 5, the photocatalyst sterilization device further comprising:

a pre-filter sieve, wherein the pre-filter sieve is arranged at a position proximal to the air inlet inside the first receiving chamber or the second receiving chamber.

8. The refrigerator according to claim 5, wherein the light source assembly comprises a first light source assembly and a second light source assembly, the first light source assembly and the second light source assembly are oppositely arranged on two sides of the photocatalyst layer.

9. The refrigerator according to claim 5, wherein a snap is arranged at an edge of the housing front wall;

an inner wall of the storage cabinet comprises a mounting slot corresponding to the snap in shape and position; and the photocatalyst sterilization device is fixed to the inner wall of the storage cabinet via the snap.

\* \* \* \* \*